United States Patent [19]
Kuchar

[11] Patent Number: 6,013,230
[45] Date of Patent: Jan. 11, 2000

[54] MULTI-FUNCTIONAL HOLDER ARTICLE AND METHOD OF USING SAME

[76] Inventor: Michael A. Kuchar, W150 N5304 Badger Dr., Menomonee Falls, Wis. 53051

[21] Appl. No.: 09/053,993

[22] Filed: Apr. 2, 1998

[51] Int. Cl.[7] .................................................. B01L 9/00
[52] U.S. Cl. ........................ 422/104; 422/99; 422/102; 600/573; 248/309.1; 248/311.2; 248/315; 220/737; 220/738; 220/752; 220/754; 220/755; 220/756; 220/757; 220/758; 220/764; 215/395; 215/396
[58] Field of Search ............................ 422/99, 102, 104; 600/573, 574, 580; 248/309.1, 311.2, 312, 312.1, 315; 206/217, 438, 569; 220/737–738, 752, 754, 755–758, 762, 763, 764; 215/395, 396, 398; D24/122, 128, 227

[56] References Cited

U.S. PATENT DOCUMENTS

| | | | |
|---|---|---|---|
| D. 304,795 | 11/1989 | Klopp | D7/70 |
| D. 306,648 | 3/1990 | Jones et al. | D24/54 |
| D. 320,331 | 10/1991 | Paone | D7/620 |
| D. 334,804 | 4/1993 | Jones et al. | D24/128 |
| D. 335,179 | 4/1993 | Jones et al. | D24/128 |
| D. 335,180 | 4/1993 | Jones et al. | D24/128 |
| D. 335,346 | 5/1993 | Jones et al. | D24/128 |
| D. 335,708 | 5/1993 | Jones et al. | D24/128 |
| D. 364,458 | 11/1995 | Jones et al. | D24/128 |
| D. 376,297 | 12/1996 | Jacobson | D7/553 |
| 2,210,972 | 8/1940 | Christenson | 211/41.2 |
| 2,628,054 | 2/1953 | Fazakerley | 248/311.2 |
| 5,096,669 | 3/1992 | Lauks et al. | 422/61 |
| 5,147,342 | 9/1992 | Kane et al. | 604/356 |
| 5,165,639 | 11/1992 | Knuppe | 248/215 |
| 5,174,965 | 12/1992 | Jones et al. | 422/102 |
| 5,202,094 | 4/1993 | Jones et al. | 422/102 |
| 5,316,732 | 5/1994 | Golukhov et al. | 422/102 |
| 5,342,330 | 8/1994 | Kane et al. | 604/329 |
| 5,422,076 | 6/1995 | Jones | 422/102 |
| 5,558,840 | 9/1996 | Jones et al. | 422/104 |

Primary Examiner—Maureen M. Wallenhorst
Attorney, Agent, or Firm—Reinhart, Boerner, Van Deuren, Norris & Riselbach, s.c.

[57] ABSTRACT

An apparatus and method for collecting a biological fluid specimen. The apparatus includes a holder article for a specimen container, wherein the holder article contains a ring which is removably engagable with a specimen container, a connector continuous with the ring, and a grasping portion continuous with the connector, the grasping portion having opposed lateral side portions which are continuous and contiguous along their entire length with one another. The grasping portion is movable along a longitudinal axis such that the lateral side portions are approachable one to another, with each side portion on an opposed side of a plane coaxial with the longitudinal axis. The connector includes a specimen collection area.

20 Claims, 4 Drawing Sheets

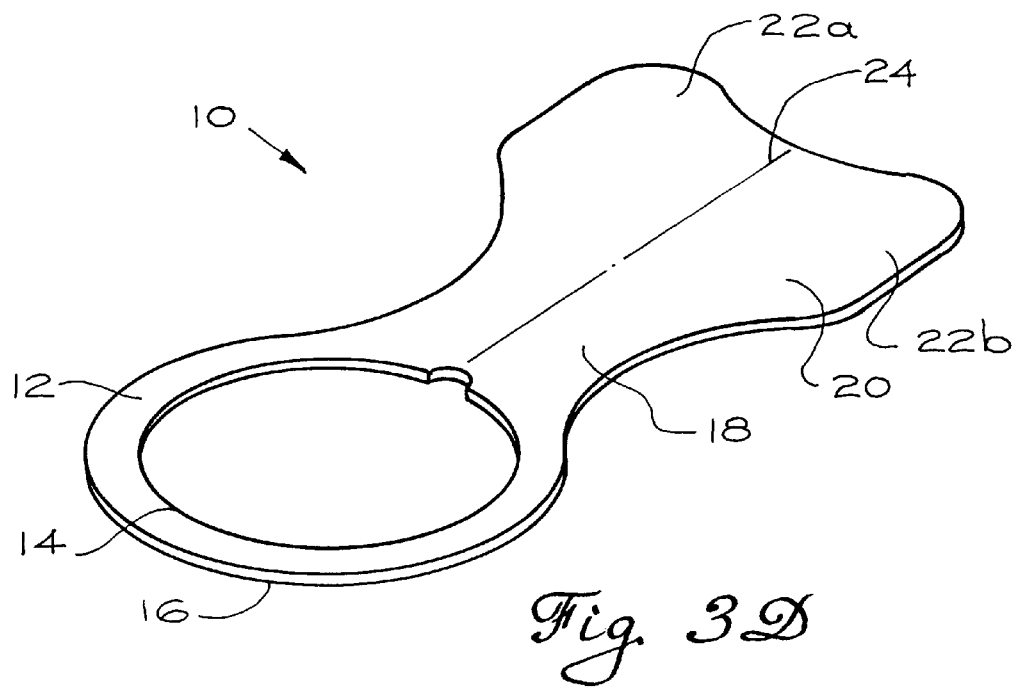
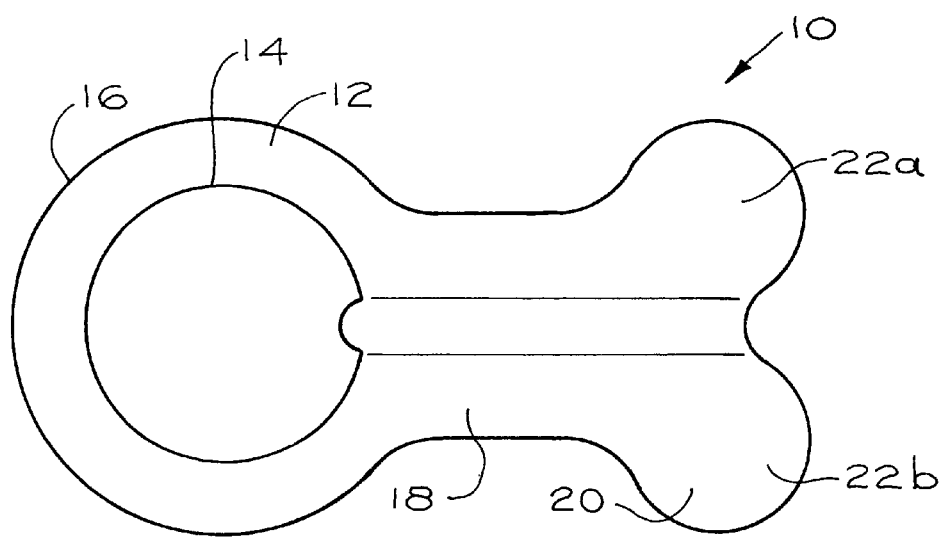

MULTI-FUNCTIONAL HOLDER ARTICLE AND METHOD OF USING SAME

BACKGROUND OF THE INVENTION

The present invention relates generally to articles for holding fluid specimen containers and, more particularly but without limitation, is directed toward such articles which can also be used to contain and/or collect errant or misdirected specimen samples.

Over the past decade, there has been an increased need and demand for analysis of various biological specimens, for purposes ranging from pregnancy testing to drug analysis. Considerable time and effort has been expended by way of devising systems and analytic techniques to ensure reliable testing and accurate results. However, relatively little effort has been devoted toward the design and development of articles to conveniently and hygienically collect such specimens. The situation is uniquely illustrated in the context of collecting urine specimens.

Typically, specimen containers and related support devices require that the container and/or device be held by the person rendering the urine specimen. Often times, a difficult situation arises through inadvertent contact with the specimen. The accompanying unpleasantness is not isolated with the specimen provider, but is shared by the health care worker or laboratory technician asked to handle or analyze the urine specimen.

The search for an efficient, economical holder device for specimen containers has been a long-standing concern in the art. Most devices utilize a long handle attached to a ring configuration which engages the specimen container. A problem arises in that the weight of the container and collected specimen poses undue stress and strain on the holder. The result is often an instability which causes errant specimen deposit or, ultimately, spillage of the entire specimen. Examples of such prior art devices are described in U.S. Pat. Nos. Des. 335,708, Des. 306,648, Des. 335,346, Des. 325,180, Des. 335,179, Des. 324,804 and 5,202,094. The last of the aforementioned patents illustrates another shortcoming of the prior art, disclosing a configuration wherein an elongated handle has a hinged connection to a ring structure, thereby introducing yet another source of structural weakness upon specimen deposit.

In summary, a considerable number of drawbacks and problems exist in the art relating to holder devices for specimen containers. There is a need for an improved holder, economically produced, to safely and efficiently collect urine specimens.

OBJECTS OF THE INVENTION

It is an object of this invention to overcome the problems and shortcomings of the prior art, including those described above. It can also be an object of this invention to provide a holder device which functions more broadly to contain, collect and transfer errant or misdirected specimens.

It can be another object of the present invention to provide a one-piece holder which is formed unitarily to impart and maintain structural integrity during use.

It can also be an object of this invention to provide a holder article which inhibits the inadvertent deposit of a specimen on the outside of an intended container.

It can also be an object of this invention to provide a method of using an article, in accordance with this invention, to direct an errant specimen, collect it, then transfer it to an intended container.

It will be understood by those skilled in the art that one or more aspects of this invention can meet certain objectives, while one or more other aspects can meet certain other objectives. Each objective may not apply equally, in all instances, to every aspect of this invention. As such, the preceding objects—in light of the prior art regarding such holder devices and specimen containers—can be viewed in the alternative with respect to any one aspect of the present invention. Other objects, features and advantages of the present invention will be apparent from the following summary and description of preferred embodiments, and as would be recognized by those skilled in the art having knowledge of specimen collection techniques and the requirements for holder articles as used in the specimen analysis industry. Such objects, features, benefits and advantages will also be apparent from the above as taken in conjunction with the accompanying figures and all reasonable inferences to be drawn therefrom.

SUMMARY OF THE INVENTION

This invention includes a new and/or improved holder article, as well as a method of using the same. The invention overcomes certain well-known problems and deficiencies, including those outlined above, while providing a cost-effective alternative to current devices. As described more fully below, the invention provides an article more user-friendly, but also more considerate and hygienic with respect to downstream health care workers and laboratory technicians.

In part, the present invention is a holder article for a specimen container of the type having an upper opening. The inventive article includes (1) a ring having a width dimension and an interior diametral dimension, with a proximate portion with respect to the user of the article, such ring removably engagable with a specimen container; (2) a connector continuous with the ring and having a width dimension; and (3) a grasping portion continuous with the connector and having opposed lateral side portions.

In preferred embodiments, the proximate portion of the ring is continuous therealong with the connector. Preferred embodiments can also include a grasping portion that is movable along a longitudinal axis thereof, such that the lateral side portions are approachable one to another, resulting with each portion positioned on opposed sides of the plane coaxial with the aforementioned longitudinal axis. In highly preferred embodiments, the connector has a width dimension greater than the interior diametral dimension of the ring. Likewise, in highly preferred embodiments, the connector is substantially non-coplanar with the ring. One or more of such structural features in combination with another provides the inventive holder article a structural stability heretofore unavailable through the prior art.

In part, the present invention also includes a method using a holder for a specimen cup to contain an errant specimen sample. The method includes (1) providing a holder having a ring removably engagable with the cup, a connector continuous with the ring, and a grasping portion continuous with the connector and having opposed lateral side portions; (2) positioning the lateral side portions of the grasping portion to provide a conduit along a line defining a longitudinal axis of the grasping portion; and (3) thereby directing an errant specimen sample along the conduit. In preferred embodiments, the lateral side portions are pre-formed to provide such a conduit. In other embodiments, such outer side portions can be moved one toward another to provide the same sort of conduit. Regardless, the conduit is preferably directed toward a specimen collection area.

As discussed more fully above, a ring with a raised interior edge and a downward flange along the outer dimension can assist in removal of an errant specimen from the collection area. A raised edge engaging a specimen cup can also operate as a guard to prevent intake from a specimen first contacting the holder article. In highly preferred embodiments, the raised edge can be configured for threaded engagement with the specimen cup. Such an engagement, alone or together with the aforementioned downward flange, operates to keep an errant specimen from soiling the outside surface of the specimen cup.

Without limitation, the present invention can also be an improvement of prior art holder articles, such an improvement including a connector continuous with both a ring and a grasping portion and configured in conjunction with the ring to provide a specimen collection area. As discussed more fully above, such an improvement can further include a grasping portion having opposed lateral side portions, with the side portions positioned such that the grasping portion provides a conduit directed toward the collection area. While preferred embodiments include side portions pre-formed to provide such a conduit, other embodiments include side portions which are approachable one to another to provide the same sort of conduit. Likewise, in preferred embodiments, the ring associated with such an improvement can be configured to facilitate movement of a specimen from the collection area. As described more fully above, such a configuration can include a raised interior edge on the ring and a downward flange continuous with the ring outer dimension, with a trough or channel therebetween.

Various embodiments of the present invention provide a unique functionality. The interior diametral dimension of the aforementioned ring can be defined by a raised edge. Such structure, in combination with a connector non-coplanar with the ring, can provide a specimen collection area. A downward flange continuous with the outer dimension of the ring can serve to prevent inadvertent specimen deposit along the outer container surface and also assist, in a drip-proof fashion, with removal of the specimen from the aforementioned collection area.

BRIEF DESCRIPTION OF THE DRAWINGS

FIG. 3C is a structural variation of the article of FIG. 3A, showing pre-formed elevated lateral side portions 22a and 22b.

FIG. 3D is an elevated perspective view of the article of FIG. 3A.

FIG. 4A is a top view of another holder article, in accordance with this invention.

DESCRIPTION OF PREFERRED EMBODIMENTS.

Figure 1A:
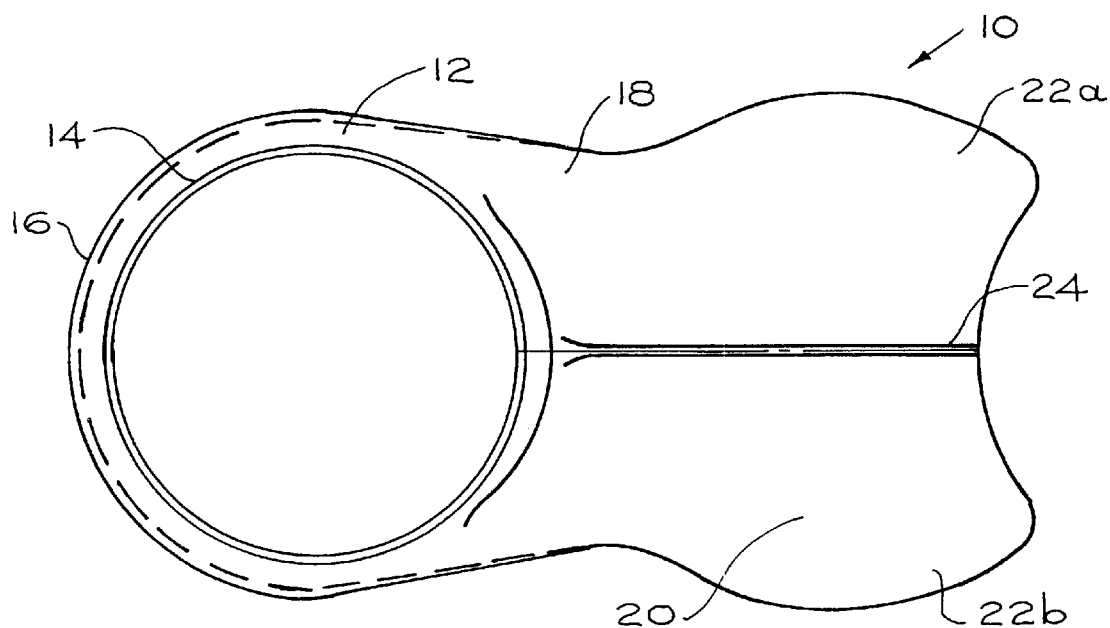
FIG. 1A is a top view of a preferred holder article, in accordance with this invention.
Figure 1B:
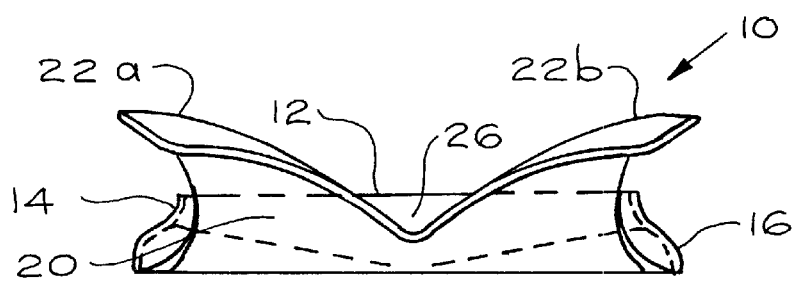
FIG. 1B is a rear view of the article shown in FIG. 1A.
Figure 1C:
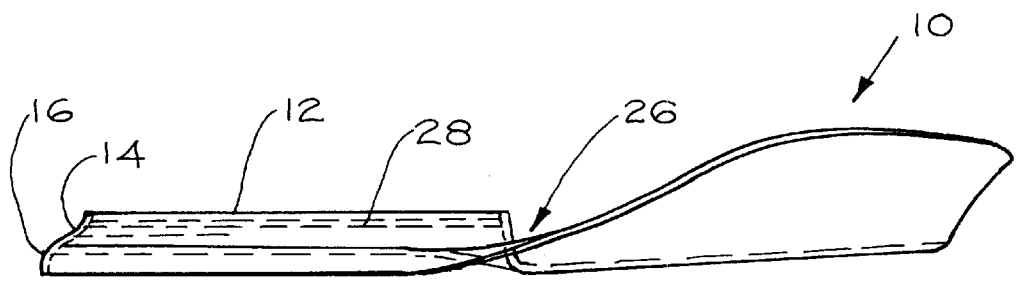
FIG. 1C is a side view of the article shown in FIGS. 1A and 1B.

A preferred embodiment of the present invention is as shown in FIGS. 1A–1C. With reference to FIG. 1A, holder article 10 includes ring 12 continuous with connector 18 which is continuous with grasping portion 20. Ring 12 has an inner diameter 14, which in preferred embodiments is a raised edge, as more clearly in FIG. 1C. Likewise, in preferred embodiments, ring 12 has an outer diameter including downward flange 16, as more clearly shown in FIGS. 1B and 1C. Grasping portion 20 includes opposed lateral side portions 22a and 22b, respectively, configured about longitudinal axis 24. As more clearly shown in FIG. 1B, the lateral side portions are positioned about longitudinal axis 24 to provide a conduit toward specimen collection area 26. With reference to FIG. 1C, area 26 and ring 12 are configured together to provide a route for specimen evacuation from area 26. While not shown in FIG. 1C, article 10 can be lifted by grasping portion 20 to permit gravity flow of the specimen from collection area 26 toward the distal portion of downward flange 16. As also shown in FIG. 1C, raised edge 14 of ring 12 can be configured with threads 28 for a mating engagement with a specimen container.

Figure 2:
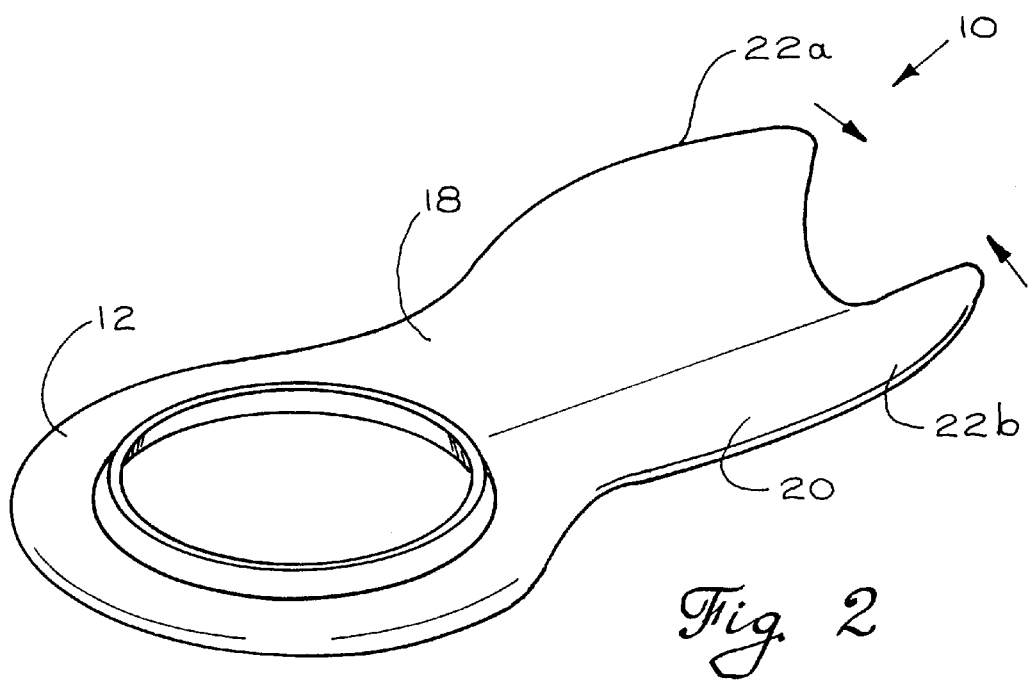
FIG. 2 is an elevated perspective view of a preferred holder article, illustrating movement of the lateral side portions from the horizontal and toward one another.
Figure 3A:
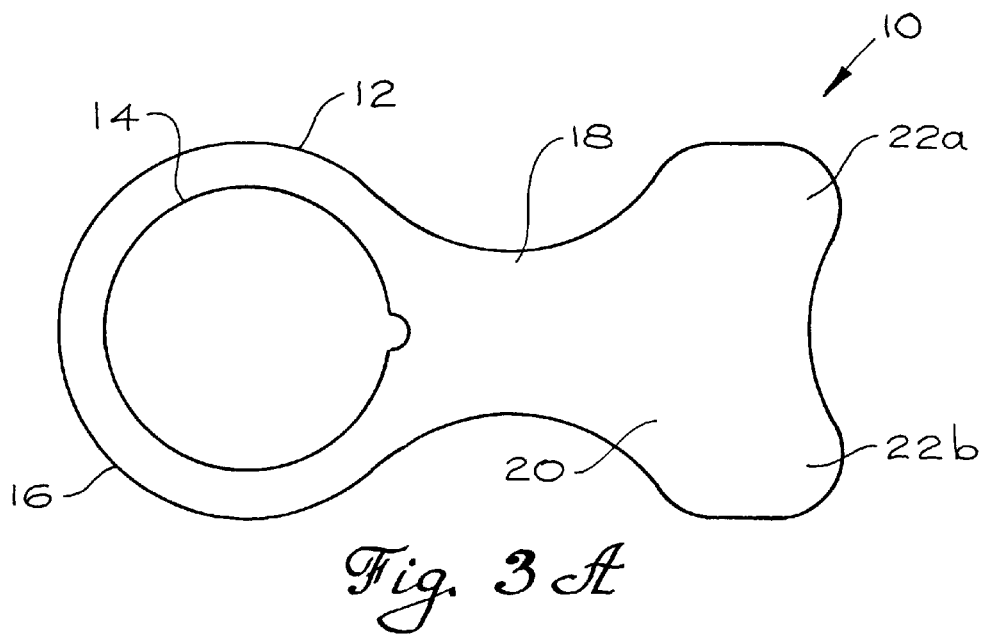
FIG. 3A is a top view of another holder article, in accordance with this invention.
Figure 3B:
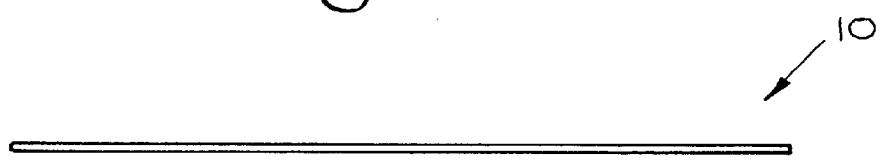
FIG. 3B is a planar side view of the article of FIG. 3A.
Figure 3B:
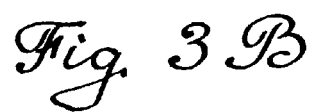
Figure 4B:
FIG. 4B is a planar side view of the article of FIG. 4A.
Figure 4C:
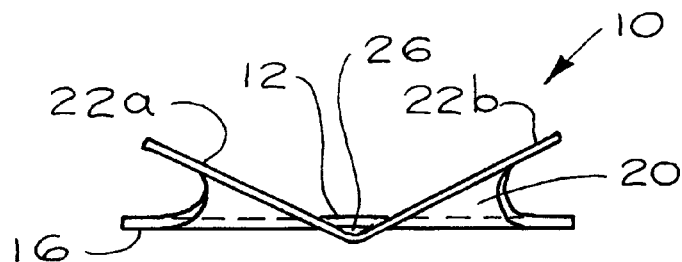
FIG. 4C is a structural variation of the article of FIG. 4A, showing pre-formed elevated lateral side portions 22a and 22b.
Figure 4D:
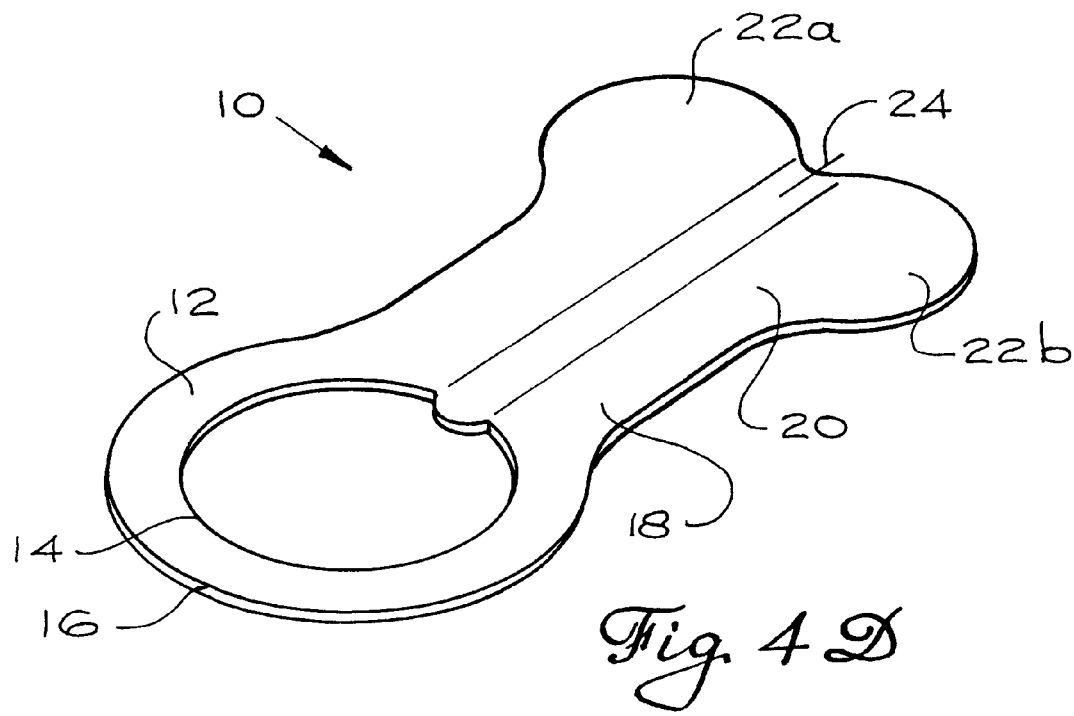
FIG. 4D is an elevated perspective view of the article of FIG. 4A.

While grasping portion 20 of the embodiment shown in FIG. 1A is pre-formed to provide an elevated arrangement of lateral side portions, it should be understood that other embodiments of the present invention provide grasping portion 20 in a substantially planar relationship with connector 18 and ring 12. With such other embodiments, grasping portion 20 is movable along a longitudinal axis such that lateral side portions 22a and 22b are approachable one to another on opposed sides of the plane coaxial with the longitudinal axis. Movement of the grasping portion in this manner, in accordance with this invention, provides a functional utility comparable to the pre-formed grasping portion shown in FIGS. 1A–1C. Specific reference is made to FIG. 2. Other such embodiments, in accordance with the present invention, are as provided in FIGS. 3A–D and 4A–D, with the structural components thereof enumerated in a manner consistent with those as provided in FIGS. 1A–1C.

The holder articles of the present invention can be prepared according to methods and processes well-known to those skilled in the art. Preferred materials include polypropylene and polyethylene, although a variety of materials can be used, including recyclable plastics. Preferred materials include those which have been shown acceptable for the testing and analytic procedures described herein. Using such materials, the present articles can be either cold-formed or heat-formed, depending upon material choice, desired article configuration and specific product parameter and performance requirements. From a manufacturing perspective, reference is again made to FIG. 1 A with particular attention to the arc of the outer diameter of ring 12 and the arc of curvature between lateral side portions 22a and 22b. Preferably, from a manufacturing perspective, both arcs have identical curvatures to minimize material waste during sequential formation of such article holders.

While the principles of this invention have been described in connection with specific embodiments, it should be understood clearly that these descriptions, along with the chosen figures and examples, are made only by way of illustration and are not intended to limit the scope of this invention in any manner. For instance, the methods and articles of this invention can be used in the veterinary sciences with equal effect. Likewise, the inventive articles can incorporate structural features to enhance stability, including without limitation ribs or indented areas along a grasping portion of such an article. Other features include those elements to facilitate engagement with a specimen container, from either side of a ring structure. Other advantages and features of this invention will become apparent from the following claims, with the scope thereof determined by usable equivalents, as understood by those skilled in the art.

I claim:

1. A holder article for a specimen container of the type having an upper circumferential opening, said article comprising:

a ring having a width dimension and an interior diametral dimension and a proximate portion, said ring removably engagable with a specimen container;

a connector continuous with said ring, said connector having a width dimension; and a grasping portion continuous with said connector, said grasping portion having a length dimensions opposed lateral side portions continuous and contiguous one with another along the entirety of said length dimension.

2. The article of claim 1 wherein said proximate portion of said ring is contiguous with said connector.

3. The article of claim 1 wherein said grasping portion is movable along a longitudinal axis thereof such that said lateral side portions are approachable one to another, each said portion on opposed sides of a plane coaxial with said longitudinal axis.

4. The article of claim 3 wherein said proximate portion of said ring is contiguous with said connector.

5. The article of claim 4 wherein said connector width dimension is greater than said ring interior diametral dimension.

6. The article of claim 1 wherein said connector is substantially non-coplanar with said ring.

7. The article of claim 1 wherein said connector includes a specimen collection area.

8. The article of claim 1 wherein said ring has a raised edge defining said interior diametral dimension.

9. The article of claim 8 wherein said edge is configured for threaded engagement with a specimen cup.

10. The article of claim 1 wherein said ring has a downward flange continuous with the width dimension of said ring.

11. A method of using a holder for a specimen cup to contain an errant specimen sample, said method comprising:

providing a holder having a ring removably engagable with a cup, a connector continuous with said ring, and a grasping portion continuous with said connector, said grasping portion having opposed lateral side portions;

positioning said lateral side portions such that said grasping portion provides a conduit along a line defining a longitudinal axis of said grasping portion; and directing an errant specimen sample along said conduit.

12. The method of claim 11 wherein said lateral side portions are moved one toward another.

13. The method of claim 12 wherein said grasping portion has a width dimension greater than said connector.

14. The method of claim 11 wherein said connector further includes a specimen collection area and said conduit is directed toward said collection area.

15. The method of claim 14 wherein said ring has a raised edge defining an interior diametral dimension.

16. The method of claim 15 wherein said ring has a downward flange continuous with a width dimension of said ring.

17. In a holder article of the type for use with a specimen container, said article having a ring removably engagable with a specimen container and a grasping portion connected to said ring, an improvement comprising a connector continuous with both said ring and said grasping portion and configured with said ring to provide a specimen collection area.

18. The holder article of claim 17 further including a grasping portion having opposed lateral side portions, said side portions positioned such that said grasping portion provides a conduit along a line defining a longitudinal axis of said grasping portion and said conduit is directed toward said collection area.

19. The holder article of claim 18 wherein said side portions are approachable one to another, each said portion on opposed sides of a plane coaxial with said longitudinal axis.

20. The holder article of claim 18 wherein said ring is configured to conduct a specimen from said collection area.

* * * * *